US009000242B2

(12) United States Patent
Lui et al.

(10) Patent No.: US 9,000,242 B2
(45) Date of Patent: Apr. 7, 2015

(54) CATALYTIC GAS PHASE FLUORINATION OF 1,1,2-TRICHLOROETHANE AND/OR 1,2-DICHLOROETHENE TO PRODUCE 1-CHLORO-2,2-DIFLUOROETHANE

(71) Applicant: Bayer Intellectual Property GmbH, Monheim (DE)

(72) Inventors: Norbert Lui, Odenthal (DE); Shanthan Rao Pamulaparthy, Hyderabad (IN); Srinivas Pvss, Hyderabad (IN); Thomas Vijaya, Hyderabad (IN); Sridhar Madabhushi, Hyderabad (IN); Rambabu Yadla, Hyderabad (IN); Narsaiah Banda, Hyderabad (IN); Sergii Pazenok, Solingen (DE)

(73) Assignee: Bayer Intellectual Property, Monheim (DE)

( * ) Notice: Subject to any disclaimer, the term of this patent is extended or adjusted under 35 U.S.C. 154(b) by 0 days.

(21) Appl. No.: 14/350,838

(22) PCT Filed: Oct. 11, 2012

(86) PCT No.: PCT/EP2012/070126
§ 371 (c)(1),
(2) Date: Apr. 10, 2014

(87) PCT Pub. No.: WO2013/053800
PCT Pub. Date: Apr. 18, 2013

(65) Prior Publication Data
US 2014/0330051 A1     Nov. 6, 2014

(30) Foreign Application Priority Data

Oct. 12, 2011   (IN) .................... 2938/2011

(51) Int. Cl.
| C07C 17/35 | (2006.01) |
| C07C 17/21 | (2006.01) |
| B01J 27/138 | (2006.01) |
| B01J 23/86 | (2006.01) |

(52) U.S. Cl.
CPC ............... C07C 17/35 (2013.01); C07C 17/21 (2013.01); B01J 27/138 (2013.01); B01J 23/866 (2013.01)

(58) Field of Classification Search
USPC ................ 502/115, 134, 183, 226, 228, 229; 570/161, 168
See application file for complete search history.

(56) References Cited

U.S. PATENT DOCUMENTS

| 4,139,568 A | 2/1979 | Baugh et al. |
| 5,932,776 A | 8/1999 | Cheminal et al. |
| 6,040,486 A | 3/2000 | Corbin et al. |
| 2002/0183569 A1* | 12/2002 | Bolmer et al. ............... 570/165 |
| 2007/0027348 A1 | 2/2007 | Quan et al. |

FOREIGN PATENT DOCUMENTS

| EP | 0502605 A1 | 9/1992 |
| EP | 2341040 A1 | 7/2011 |
| WO | 9216479 A1 | 10/1992 |
| WO | 2008030442 A1 | 3/2008 |

OTHER PUBLICATIONS

Rao et al. "Effect of Acid Strength of Co-Precipitated Chromia/Alumina Catalyst on the Conversion and Selectivity in the Fluorination of 2-Chloro-1,1,1-Trifluoroethane to 1,1,1,2-Tetrafluoroethane", Journal of Fluorine Chemistry 95 (1999) 177-180.

* cited by examiner

*Primary Examiner* — Shilendra Kumar
(74) *Attorney, Agent, or Firm* — Miles & Stockbridge P.C.

(57) ABSTRACT

The invention is directed to a catalyst for the gas phase fluorination of 1,1,2-trichloroethane and/or 1,2-dichloroethene with HF to give 1-chloro-2,2-difluoroethane which catalyst is prepared by co-depositing $FeCl_3$ and $MgCl_2$ on chromia-alumina, or co-depositing $Cr(NO_3)_3$ and $Ni(NO_3)_2$ on active carbon, or by doping alumina with $ZnCl_2$, and to a process for the preparation of 1-chloro-2,2-difluoroethane comprising a catalytic gas phase fluorination of 1,1,2-trichloroethane and/or 1,2-dichloroethene wherein one of the catalysts according to claim 2 or 3 is used.

12 Claims, No Drawings

CATALYTIC GAS PHASE FLUORINATION OF 1,1,2-TRICHLOROETHANE AND/OR 1,2-DICHLOROETHENE TO PRODUCE 1-CHLORO-2,2-DIFLUOROETHANE

CROSS REFERENCE TO RELATED APPLICATIONS

This application is a §371 National Stage Application of PCT/EP2012/070126, filed Oct. 11, 2012 which claims priority of IN 2938/2011, filed Oct. 12, 2011.

BACKGROUND

1. Field of the Invention

The present invention relates to a catalytic gas phase (vapor phase) fluorination of 1,1,2-trichloroethane (140 or TCE) and/or 1,2-dichloroethene (1130 or DCE) using hydrogen fluoride (HF) to produce 1-chloro-2,2-difluoroethane (i.e. 1,1-difluoro-2-chloroethane or 142), as well as to the catalysts used in said gas phase fluorination.

2. Description of Related Art

1-Chloro-2,2-difluoroethane is known to be useful as a foam blowing agent and can be employed as a starting material in the preparation of agrochemicals or pharmaceuticals (cf. PCT/EP2011/059691). Several methods for the preparation of hydrocarbon fluorides in the gas phase are known (cf. WO 01/74483 and the prior art mentioned therein).

FR 2 783 820 A1 describes, for example, a method for the preparation of 142. In this preparation method 1,1,1-trichloroethane (T112) is fluorinated with HF in the gas or liquid phase. The gas phase reaction is conducted at a temperature between 120° C. and 400° C. using a solid chrome catalyst or a chrome catalyst deposited on carbon, $Al_2O_3$, or $AlF_3$, or deposited on an oxyfluorinated aluminum support. The reaction of T112 with HF to T142 in the gas phase gave 78% of T142 at a conversion rate of T112 of 100%. The catalyst used for this reaction is said to consist of 58.6% fluorine, 25.9% aluminum, 6.4% nickel, 6.0% chrome and 3.1% oxygen. The density parameter of said catalyst is given to be 0.85 g/mL and the BET surface was 23 $m^2/g$.

EP 1 008 575 A1 (which is an equivalent of US 2002/0183569 A1 and U.S. Pat. No. 6,063,969 B) describes a catalytic gas phase fluorination of 140 with HF for preparing 142. The catalyst can be supported or unsupported. It is preferred to use a fluorinated salt of chromium oxide ($Cr_2O_3$). In the example given therein, unsupported $Cr_2O_3$ is used and turned into a fluorinated salt by co-feeding a mixture of HF and air over the catalyst bed for 18 hours at 380° C. The catalytic gas phase fluorination according to the example given in this document was conducted with the following parameters: the molar ratio of HF: 140 was 7.8:1, the reaction temperature was 220° C., the pressure was 150 psi (~10 bar), and the contact time was 34 seconds, leading to a 100% conversion of 140 with a selectivity of 70.2% for 142.

EP 1 008 574 A1 describes a catalytic gas phase fluorination of 1,2-dichloroethene (1130) for preparing 142 in the presence of a catalyst. The catalyst is preferably a supported or unsupported fluorinated salt of antimony (in particular $SbCl_5$). In the example 1—similar to EP 1 008 575 A1—unsupported $Cr_2O_3$ was turned into a fluorinated salt by co-feeding a mixture of HF and air over the catalyst bed for 18 hours at 380° C. The catalytic gas phase fluorination according to the example 1 was then conducted with the following parameters: the molar ratio of HF:1130 was 6.5:1, the reaction temperature was 220° C., the pressure was 150 psi (~10 bar), the contact time was 34 seconds, leading to a 88.3% conversion of 1130 with a selectivity of 84.2% for 142.

In the example 2 of EP 1 008 574 A1 a $SbCl_5$ catalyst on active carbon was activated at 50° C. by co-feeding a mixture of HF and nitrogen over the catalyst bed for 18 hours to give the fluorinated salt. The catalytic gas phase fluorination according to the example 2 was then conducted with the following parameters: the molar ratio of HF: 1130 was 6.5:1, the reaction temperature was 120° C., the pressure was 120 psi (~8 bar), the contact time was 34 seconds leading to a 95% conversion of 1130 with a selectivity of 94.9% for 142.

When looking for an efficient way for the preparation of 1-chloro-2,2-difluoroethane in a large scale the inventors found that the use of the catalysts described in EP 1 008 574 A1 or EP 1 008 575 A1 is not satisfactory. In particular, the published conversion rates and the selectivity towards the preparation of 142 could not be reproduced with the described fluorination system (cf. examples B1 and B2 herein).

SUMMARY

It was thus desirable to find a selective process for the preparation of 142 with which a good productive output by volume can be achieved and which minimizes the need for purification operations after the fluorination process and to find suitable catalysts for the preparation of 142.

The inventors now found a process for the preparation of 1-chloro-2,2-difluoroethane (142) starting from 1,1,2-trichloroethane (140) as well as specific catalysts with which a high conversion rate of the starting product 140 and, notably, also of the main intermediate, namely 1,2-dichloroethene (1130), can be achieved. This combined selectivity of these catalysts towards the intermediate 1130 and the product 142 is particularly advantageous for carrying out the process according to the invention in a continuous mode and securing a high and efficient output of 142. By carrying out the process according to the invention and using the catalysts according to the invention no remarkable under- or over-fluorination occurred.

The present invention therefore relates to a process for the preparation of 1-chloro-2,2-difluoroethane (142) comprising a catalytic gas phase fluorination of 1,1,2-trichloroethane using one of the catalysts according to the invention, whereas the catalyst has been fluorinated before being used.

DETAILED DESCRIPTION OF A PREFERRED EMBODIMENT

In an embodiment of the process according to the invention 140 or 1130 are fluorinated by HF to give 1-chloro-2,2-difluoroethane (142) under the conditions described herein.

In another embodiment of the process according to the invention 140 and 1130 are simultaneously fluorinated by HF in the reactor under the conditions described herein, whereas the feeding of 140 and 1130 into the reactor is done over separate feeding lines.

The present invention further relates to catalysts which are prepared by co-depositing $FeCl_3$ and $MgCl_2$ on chromia-alumina, or co-depositing $Cr(NO_3)_3$ and $Ni(NO_3)_2$ on active carbon, or by doping alumina with $ZnCl_2$. It is understood that before mentioned salts can be used as salt hydrates as exemplified in the examples. Any reference to before mentioned salts thus includes their salt hydrates.

The process according to the invention is preferably carried out in a continuous mode (continuously). The inventors found that the activity of the catalysts according to the invention lasts for several days (e.g. more than 400 hours). This is a key feature for a catalyst being suitable to be used in a continuous process. Over the course of a reaction, catalysts may get poisoned through side products of the reaction, grime or small carbon-containing molecules which are a result of the decomposition of the starting materials, the desired product or the side products.

It is known that the degree of the conversion in a process and the selectivity of a catalyst depend on the residence time (contact time) which determines the W/F value, i.e. the catalyst weight/flow rate of raw materials in moles. It was found that the preferred W/F value in the fluorination of 140 to 142 is in the range of 100 to 300, preferably in the range of 200 to 250; and in the fluorination of 1130 to 142 the W/F value in the range of 250 to 500, preferably in the range of 300 to 450, most preferably is in the range of 300 to 400.

The contact time in the present reaction can range from about 10 to about 200 seconds, preferably from about 50 to about 130 seconds. A long contact time often results in the formation of a remarkable amount and number of side products and a short contact time may result in a lower conversion rate and thus a less effective reaction.

The catalysts according to the invention can be used in every shape, such as spheres, tablets or extrudes. The shape of the catalyst often depends on the shape of the support. Extrudes are often small sized pellets (e.g. having sizes of about 2.5 mm) which can be prepared by known methods. The shape of the catalyst has no effect on its activity.

Before employed in the process according to the invention, the catalyst is pre-treated and activated before use.

For the pre-treatment, the catalyst is loaded into the reactor. Nitrogen gas is passed over the bed of catalyst starting at a temperature of 120° C. and gradually increasing the temperature to about 400° C. The reactor is maintained at this temperature for 1 to 50 hours, preferably for 5 to 30 hours, more preferably for 24 hours. The contact time may vary. Preferably the contact time is in the range of about 1 to about 100 seconds, preferably in the range from about 10 to about 40 seconds.

After pre-treatment, the temperature in the reactor is lowered to a temperature of about 150° C. Then, the activation agent alone or together with an inert gaseous carrier, such as air or nitrogen, is fed over the catalyst bed. During this first step of the activation of the catalyst, an exothermic reaction can take place and water can evolve. By adjusting the flow rates of the activation agent and/or the inert gaseous carrier the temperature of the catalyst bed is controlled so that it does not exceed 400° C. When the water evolution ceased and the exothermic reaction stopped, which can take about 20 to 30 hours, the temperature of the catalyst bed is slowly brought to about 375° C. The feeding of the reactor with the inert gaseous carrier can now be stopped and the activation of the catalyst, which is basically the fluorination of the catalyst with the activation agent (preferably with HF) is continued for a period of about 15 to about 40 hours, preferably from about 20 to about 30 hours at about 375° C. The activation is completed when the moisture content of the activation is below a certain threshold, preferably 1% (v/v). The catalyst is now activated and ready to be used in the process according to the invention.

The bed temperature of the catalyst is then lowered to a temperature in the range of about 180 to 300° C., preferably about 200° C., and the system is pressurized by closing the reactor exit valve to obtain about 3 to 4 bar (which is 3-4 kg) pressure.

The activating agent is an agent which is able to fluorinate the catalyst. The activation agent is preferably HF. If HF is used, then it can be fed to the system as a gas or a liquid. If fed as a liquid, it is essential that the reaction set-up comprises an evaporator. In the first part of the activation step as given above, HF is preferably fed over the catalyst bed as a mixture of approximately equal volumes HF and inert gaseous carrier (in particular air or nitrogen). The concentration of HF in air or nitrogen can range from about 1 to 20 mole-% HF.

The fluorination reaction according to the invention can be initiated by introducing HF, 140 and/or 1130 into an evaporator, whereas the feed quantity of HF 140 and/or 1130 are adjusted to give the desired molar ratios and the contact time(s). 140 and HF are preferably introduced by two independent lines. 1130 can be introduced together with 140 or by another independent line. The resulting gaseous mixture is then allowed to enter the reactor at the required reaction temperature and pressure.

The reactor is normally a tubular reactor which is loaded with catalyst, whereas the catalyst forms the so-called catalyst bed.

Advantageously, the reaction temperature and the pressure are maintained during the course of the gas phase fluorination. The desired end product 142 and the intermediate 1130 is thus prepared and this product stream which contains also HF is then allowed to exit the reactor to be separated from unwanted side products of the reaction and unreacted starting materials such as HF. In the process according to the invention, 1130 and HCl are the only side products which occur in remarkable amounts.

The product stream is then scrubbed, which means the stream is passed/guided into a cooler which contains water at a temperature of about 0° C. to 5° C. to remove unreacted HF, and HCl which is formed during the reaction. The organic layer formed in the cooler, which contains the desired 142, is separated from the aqueous layer, washed with water and dried with sodium sulfate and analyzed using gas chromatography.

For the continuous process 1130 and 140 are separated from 142 and then gated to be fed to the reactor to fuel the continuous process. Separation can be done by distillation in a glass column. If distillation is used, then reacting under pressure has the additional advantage of directly feeding the product stream into distillation columns which also operate under pressure, for the separation of 140 and 1130 and to recover and recycle the unreacted starting materials HF and 140.

In the process according to the invention the molar ratio of HF to 140 and/or 1130 is in the range from about 2:1 and 30:1. Preferably the molar ratio of HF to 140 and/or 1130 lies in the range from about 3:1 to about 12:1.

The process according to the invention can be carried out at temperature ranging from about 200° C. to about 350° C., preferably from about 200° C. to about 300° C. and it can be carried out at normal or elevated pressure. The operating pressure can be up to 25 bar. Preferably, the operating pressure is in the range from about 4 to about 20 bar.

EXAMPLES

Catalyst Preparation

All chemicals used are of commercial grade. Demineralized water (DM water) is used throughout. If not mentioned otherwise room temperature refers to temperatures around 28° C.

[Catalyst A]—Amorphous Chromia $Cr_2O_3$ Used as Extrudes (Pellets)

An aqueous solution of chromium trioxide is prepared by slow dissolution of 1.04 kg $CrO_3$ in 12.6 kg water and continuous stirring in a steam jacketed SS (stainless steel) vessel. Ethyl Alcohol (1.5 liter) is added at regular intervals to the chromium trioxide solution taking care to see that the exothermicity is well under control. The reaction mixture is brought to reflux at 100° C. The refluxing is continued till all the chromium trioxide is reduced as indicated by the appearance of a dark brown gel. The reactor is cooled and the slurry transferred to a rate-cone evaporator unit for concentrating the gel. The moist cake (1.1 kg) was discharged, dried and powdered in a pot mill A portion of the powdered catalyst was extruded. The extrudes were calcined at 400° C. in nitrogen atmosphere. The surface area is measured being in the range of 200-230 $m^2/g$. The X-ray analysis indicates amorphous nature.

[Catalyst B]—Amorphous Chromia-Alumina ($Cr_2O_3/Al_2O_3$)

An aqueous solution of $Cr(NO_3)_3 9H_2O$ (820 g) in 3 kg DM water and $Al(NO_3)_3 9H_2O$ (3.46 kg) in 10 kg DM water was prepared separately under stirring and mixed together followed by further dilution with 17 kg of DM water. Diluted ammonia solution (10%) was prepared and discharged at the rate of 10 g/min for a period of 8-10 hours to the above metal ion solution. The precipitation was observed from pH 3.3 and the addition of ammonia solution was contained until the pH of the slurry reaches 7.8. The slurry was heated at 90° C. for 3 hours and filtered. The wet cake was washed with hot water (2 kg) followed by cold water (2 kg) and partially dried at 70° C. and extruded through a 4 mm dye. The catalyst extrudes dried (500 g) in hot air oven at 90° C. for 1 hour and at 100° C. for 2 hours. Finally the catalyst extrudes were calcined at 400° C. for 22 hours under nitrogen blanket. The surface area of the catalyst was found to be in the range of 250-300 $m^2/g$. The X-ray analysis indicates amorphous nature.

[Catalyst C]$Cr_2O_3/Al_2O_3/FeCl_3/MgCl_2$—According to the Invention:

A mixture of 5.98 g $FeCl_3$ (97%) (0.0368 moles) and 14.85 g $MgCl_2 7H_2O$ (0.0671 moles) is dissolved in 40 g distilled water and added to 80 g of the amorphous Chromia-Alumina ($Cr_2O_3/Al_2O_3$) extrudes described as Catalyst B and slowly stirred at room temperature for 3 to 4 hours. The excess of water is removed under vacuum and the resulting catalyst is dried in an oven at 130° C. for 12-15 hours until constant weight. The surface area of the catalyst was found to be 78 $m^2/g$. The X-ray analysis indicates amorphous nature.

[Catalyst D]$Al_2O_3/ZnCl_2$—According to the Invention:

100 g of commercially available γ-$Al_2O_3$ extrudes are suspended in a solution of 5 g $ZnCl_2$ (0.0368 moles) in DM water (40 g) and stirred for 2-3 h. The excess of water is removed under vacuum and the resulting catalyst is dried in an oven at 130° C. for 10 to 12 hours until constant weight. The surface is determined to be 191.26 $m^2/g$ and the X-ray diffractions analysis indicates amorphous nature.

[Catalyst E]$Cr_2O_3$ (20%)—Ni (5%) on Carbon—According to the Invention 317.4 g (0.793 moles) $Cr(NO_3)_3$ x 9 $H_2O$ and 50.05 g (0.172 moles) $Ni(NO_3)_2$ x 6 $H_2O$ (99%) are dissolved in 125 g distilled water. 150 g commercially available active carbon extrudes are added. The suspension is slowly stirred for 2 to 3 hours at room temperature. The excess water is removed under vacuum and dried in an oven at 130° C. for 24 hours until constant weight. The surface is determined to be 372 $m^2/g$ and the X-ray diffractions analysis indicates amorphous nature.

[Catalyst F]$Cr_2O_3$ (20%)—Ni (10%)—According to the Invention 154.16 g (0.385 moles) $Cr(NO_3)_3$ x 9 $H_2O$ and 49.55 g (0.170 moles) $Ni(NO_3)_2$ x 6 $H_2O$ (99%) are dissolved in 100 g distilled water. 70 g commercially available active carbon extrudes are added. The suspension is slowly stirred for 2 to 3 hours at room temperature. The excess water is removed under vacuum and dried in an oven at 130° C. for 24 hours until constant weight. The surface is determined to be 73 $m^2/g$ and the X-ray diffractions analysis indicates amorphous nature.

In the tables, the following abbreviations are used: T=reaction temperature; P=pressure; ratio=mole ratio of HF and TCE ; CT=contact time; RT=reaction time; 140 or TCE=1,1,2-trichloroethane; 1130 or DCE=1,2-dichloroethene; 142=1-chloro-2,2-difluoroethane.

General Method of Fluorination

The experimental set up consists of separate feed lines for HF and 140 and/or 1130, an evaporator, and a 100 cm long inconel tubular reactor loaded with catalyst having a diameter of one inch (1"=2.54 cm), a pressure relief trap, a regulating value at the exit of the reactor, a cooler containing water, a drier, and a receiver. A sample of the low volatile product stream is drawn periodically from a sampling valve between the drier and receiver. The temperatures in different zones are maintained by electrically heated block furnaces and PID controller.

The catalyst is loaded into the tubular reactor and pretreated with nitrogen at 400° C. for 24 hours. The temperature is then lowered to 150° C. and a slow stream of HF is introduced along with nitrogen. After the initial exothermic reaction, nitrogen is slowly withdrawn while raising temperature of the catalyst bed to 375° C. The fluorination is continued until the moisture content in the exit HF is below 1% (about 18 to 20 hours). The bed temperature of the catalyst is then brought to 200° C. and slowly the system was pressurized by closing the reactor exit valve to attain 3-4 kg pressure. The fluorination reaction was initiated by introducing 140 and/or 1130 into the system along with HF. The feed quantity of HF and 140 and/or 1130 were adjusted to give the desired molar ratios and the contact time. The product stream is scrubbed (washed) with water maintaining 0-5° C. by external ice cooling. The product is collected as an organic layer in the cooler. The undissolved acid free organic vapor escapes from the cooler into the drier and finally captured in the receiver which is cooled in dry ice-acetone. The organic layer in the cooler was separated, washed with cold water and dried with sodium sulfate. The composition of the product stream in the organic layer is determined by gas chromatography after reaching steady state and is based on peak areas. The fluorination experiments where carried out under pressure as indicated in the examples below.

A: Examples According to the Invention

A1. Fluorination of 1,1,2-trichloroethane (140, TCE) with HF on Catalyst C

| Sample No. | T [° C.] | p [bar] | ratio HF/140 | HF [g] | 140 [ml] | CT [sec] | Conversion of 140 [%] | Selectivity to 142 | Selectivity to 1130 | RT [hour] |
|---|---|---|---|---|---|---|---|---|---|---|
| 1 | 220 | 5 | 6.6 | 24.1 | 17 | 90 | 90.1 | 22.4 | 54.1 | 4.5 |
| 2 | 240 | 5 | 6.5 | 22.4 | 16 | 87 | 98.1 | 39.3 | 45.1 | 4 |

A2. Fluorination of 1,1,2-trichloroethane (140, TCE) with HF on Catalyst D

| Sample No. | T [° C.] | p [bar] | ratio HF/140 | HF [g] | 140 [ml] | CT [sec] | Conversion of 140 [%] | Selectivity to 142 | Selectivity to 1130 | RT [hour] |
|---|---|---|---|---|---|---|---|---|---|---|
| 1 | 220 | 5 | 8.69 | 27.3 | 14.6 | 127 | 92.5 | 34.8 | 47.8 | 4 |
| 2 | 240 | 5 | 7.3 | 22.9 | 14.5 | 142 | 97.1 | 26.3 | 61.5 | 4 |

A3. Fluorination of 1,1,2-trichloroethane (140, TCE) with HF on Catalyst E

| Sample No. | T [° C.] | p [bar] | ratio HF/140 | HF [g] | 140 [ml] | CT [sec] | Conversion of 140 [%] | Selectivity to 142 | Selectivity to 1130 | RT [hour] |
|---|---|---|---|---|---|---|---|---|---|---|
| 1 | 230 | 5 | 7.9 | 30.1 | 17.6 | 135 | 94.1 | 64.8 | 29.8 | 4 |
| 2 | 240 | 5 | 8.9 | 35.4 | 18.5 | 114 | 98.9 | 64.4 | 28.6 | 4 |
| 3 | 240 | 5 | 8.4 | 42.3 | 23.2 | 94 | 99.2 | 65.5 | 27.2 | 4 |
| 4 | 240 | 6 | 7.3 | 38.7 | 24.5 | 102 | 98.8 | 51 | 38.8 | 4 |

A4. Fluorination of 1,2-dichloroethene (1130, DCE) with HF on Catalyst E

| Sample No. | T [° C.] | p [bar] | ratio HF/1130 | HF g | DCE ml | CT [sec] | Conversion of 1130 [%] | Selectivity to 142 | RT [hour] |
|---|---|---|---|---|---|---|---|---|---|
| 1 | 240 | 5 | 5.6 | 13 | 11.2 | 139 | 60.6 | 99.6 | 2 |
| 2 | 240 | 7 | 6.6 | 24.2 | 17.6 | 160 | 57.1 | 93.4 | 3 |
| 3 | 255 | 5 | 7.2 | 20.9 | 13.7 | 130 | 63.8 | 93.4 | 3 |

A5. Fluorination of 1,2-dichloroethene (1130, DCE) with HF on Catalyst E with 2 parallel reactors

| Sample No. | T [° C.] | p [bar] | ratio HF/1130 | HF [g] | 1130 [ml] | CT [sec] | Conversion of 1130 [%] | Selectivity to 142 | RT [hour] |
|---|---|---|---|---|---|---|---|---|---|
| 1 | 230 | 5 | 10.6 | 33.8 | 15.5 | 102 | 75.3 | 97 | 4 |
| 2 | 230 | 5 | 10.5 | 33.2 | 15.3 | 91 | 83.2 | 99 | 4 |
| 3 | 245 | 5 | 7.7 | 29 | 18.3 | 101 | 80.3 | 98.9 | 4 |

A6. Fluorination of 1,1,2-Trichloroethane (TCE) with HF on Catalyst F

| Sample No. | T [° C.] | p [bar] | ratio HF/1130 | HF [g] | 1130 [ml] | CT [sec] | Conversion of 1130 [%] | Selectivity to % 142 | Selectivity to % 1130 | RT [hour] |
|---|---|---|---|---|---|---|---|---|---|---|
| 1 | 240 | 5 | 8.2 | 36.6 | 20.5 | 87.9 | 99.38 | 51.33 | 42.69 | 4 |
| 2 | 240 | 5 | 8.2 | 38.3 | 21.8 | 83.9 | 100 | 40.76 | 53.47 | 4 |
| 3 | 260 | 5 | 8.4 | 40.7 | 22.32 | 76.3 | 97.59 | 41.42 | 51.66 | 4 |
| 4 | 260 | 5 | 8.0 | 34.2 | 20.0 | 78.89 | 98.53 | 40.33 | 54.79 | 3.5 |

B: Examples using known catalysts A or B:
B1. Fluorination of 1,1,2-trichloroethane (140, TCE) with HF on Catalyst A (cf. EP 1 008 575 A1)

| Sample No. | T [° C.] | p [bar] | ratio HF/140 | CT [sec] | Conversion of 140 [%] | Selectivity to 142 | Selectivity to 1130 | RT [hour] |
|---|---|---|---|---|---|---|---|---|
| 1 | 220 | 9 | 22.9 | 49.1 | 31.0 | 3.9 | 86.7 | 4.5 |
| 2 | 255 | 9 | 9.1 | 85.7 | 58.0 | 15.3 | 72.22 | 4 |
| 3 | 280 | 9 | 11.5 | 88.4 | 63.1 | 12.04 | 72.10 | 3 |

The results are in contrast to the teaching of EP 1 008 575 A1, which suggests that by using bulk $Cr_2O_3$ (chromia) such as Catalyst A, a high conversion of TCE and high selectivity towards the formation of 142 could be achieved.

B2. Fluorination of 1,1,2-trichloroethane (140, TCE) with HF on Catalyst B

| Sample No. | T [° C.] | p [bar] | ratio HF/140 | CT [sec] | Conversion of 140 [%] | Selectivity to 142 | Selectivity to 1130 | RT [hour] |
|---|---|---|---|---|---|---|---|---|
| 1 | 250 | 10 | 14.3 | 183 | 92.9 | 23.7 | 61.4 | 6 |
| 2 | 270 | 10 | 10.5 | 174 | 73 | 16 | 71 | 3 |
| 3 | 285 | 10 | 12.4 | 233 | 92.5 | 24.4 | 65.3 | 5 |

The invention claimed is:

1. A process for preparation of 1-chloro-2,2-difluoroethane comprising a catalytic gas phase fluorination of 1,1,2-trichloroethane comprising using a catalyst which is prepared by co-depositing $FeCl_3$ and $MgCl_2$ on chromia-alumina and which has been fluorinated by treating the catalyst with a fluorine containing activation agent at a temperature not exceeding 400° C.

2. The process according to claim 1, wherein the catalyst has been fluorinated by HF as activation agent.

3. A process for preparation of 1-chloro-2,2-difluoroethane comprising a catalytic gas phase fluorination of 1,2-dichloroethene comprising using a catalyst which is prepared by co-depositing $FeCl_3$ and $MgCl_2$ on chromia-alumina and which has been fluorinated by treating the catalyst with a fluorine containing activation agent at a temperature not exceeding 400° C.

4. A process for preparation of 1-chloro-2,2-difluoroethane comprising a catalytic gas phase fluorination of 1,1,2-trichloroethane and 1,2-dichloroethene, comprising using a catalyst which is prepared by co-depositing $FeCl_3$ and $MgCl_2$ on chromia-alumina and which has been fluorinated by treating the catalyst with a fluorine containing activation agent at a temperature not exceeding 400° C. and wherein 1,1,2-trichloroethane and 1,2-dichloroethene are fed separately to a reactor.

5. The process according to claim 1, wherein contact time is in a range from 10 to 200 seconds.

6. The process according to claim 1, wherein reaction temperature is in a range from 200° C. to 350° C.

7. The process according to claim 3, wherein the catalyst has been fluorinated by HF as activation agent.

8. The process according to claim 4, wherein the catalyst has been fluorinated by HF as activation agent.

9. The process according to claim 3, wherein contact time is in a range from 10 to 200 seconds.

10. The process according to claim 3, wherein reaction temperature is in a range from 200° C. to 350° C.

11. The process according to claim 4, wherein contact time is in a range from 10 to 200 seconds.

12. The process according to claim 4, wherein reaction temperature is in a range from 200° C. to 350° C.

* * * * *